United States Patent [19]

Negersmith

[11] 4,130,394

[45] Dec. 19, 1978

[54] SHORT SAMPLE DETECTION

[75] Inventor: Kent M. Negersmith, Carmel, N.Y.

[73] Assignee: Technicon Instruments Corporation, Tarrytown, N.Y.

[21] Appl. No.: 839,146

[22] Filed: Oct. 3, 1977

[51] Int. Cl.² ............................................. G01N 1/14
[52] U.S. Cl. ............................ 23/230 R; 73/425.4 R; 422/58; 422/100
[58] Field of Search .................. 23/230 R, 253 R, 259; 73/425.4 R, 425.6

[56] References Cited

U.S. PATENT DOCUMENTS

| | | | |
|---|---|---|---|
| 3,419,358 | 12/1968 | Smythe et al. | 23/253 R |
| 3,484,170 | 12/1969 | Smythe et al. | 23/253 R |
| 3,572,996 | 3/1971 | Reichler et al. | 23/230 R |
| 3,843,326 | 10/1974 | Lichtenstein | 23/259 |
| 4,015,938 | 4/1977 | Jay | 73/425.6 |

Primary Examiner—R.E. Serwin
Attorney, Agent, or Firm—S. P. Tedesco; Robert S. Salzman

[57] ABSTRACT

A dilutor/dispenser system wherein a marker, e.g., an air bubble, is introduced at the probe inlet prior to each aspiration cycle, so as to be displaced along the probe system during such cycle. The location of the marker is detected at the end of the aspiration cycle, to indicate whether an appropriate liquid volume has been aspirated. The aspirated liquid, along with the marker and a predetermined volume of diluent, is subsequently dispensed. An alarm may be activated, if an improper volume has been aspirated.

20 Claims, 7 Drawing Figures

SHORT SAMPLE DETECTION

BACKGROUND OF THE INVENTION

1. Field of the Invention

This invention relates generally to a dilutor/dispenser system for reliably dispensing precise predetermined volumes of successive liquid samples.

2. Description of Prior Art

A variety of different systems has been developed for analyzing liquid samples. Each such system requires that a predetermined volume of sample, which may be diluted, be reacted with a precise volume of reagent, to produce a reaction product indicative of the concentration of a particular constituent being analyzed. Present-day systems are classified as being of the continuous- or discrete-type. A continuous-type system has been described, for example, in U.S. Pat. No. 3,241,432, issued on Mar. 22, 1966 and assigned to a common assignee. In such a system, samples are successively introduced as a flowing stream into the system by means of an aspirating probe. Such samples are divided into a plurality of aliquots. The sample aliquots are directed, in phase, along individual conduits, wherein each is appropriately diluted and mixed with one or more selected reagents, in online fashion, so as to be reacted with respect to a particular constituent. The reacted sample aliquots are passed through appropriate reaction detectors, such as colorimeters for color-sensitive reactions, etc., and the analytical results are subsequently recorded in correlated fashion. In such systems, proper sample volumes are ensured by precisely controlling the rate and duration of the sample aspiration. In a discrete- or batch-type system, such as described in U.S. Pat. No. 3,971,630, issued on July 27, 1976 and assigned to a same assignee as the present invention, measured volumes of sample (appropriately diluted) and appropriate reagents, to effect a particular reaction, are introduced into an individual reaction cell. The reaction mixture is then analyzed, e.g., colorimetrically either in the reaction cell or by flowing the reaction mixture through an appropriate reaction detector. Regardless of the system type, it is essential for obtaining accurate results that a proper volumetric ratio be maintained between the liquids being reacted, so that the concentration of the particular constituent being analyzed can be properly related to an absolute standard. Any variation in such ratio, obviously, would not allow proper relating of the analytical results with such standard.

The present invention is particularly intended for use in systems of the discrete-type, wherein the sample is not aspirated directly into the system. In such systems, sample introduction and dilution are usually effected by a dilutor/dispenser unit, which is a liquid-delivery instrument capable of precisely dispensing small sample volumes, appropriately diluted. The probe of the dilutor/dispenser unit is immersed into a sample receptacle, often hand-held by the technician, to aspirate a predetermined sample volume into the probe, against a volume of diluent. Subsequently, the aspirated sample volume, along with a predetermined volume of a diluent, are dispensed into a reaction cell, which may contain or subsequently receive a predetermined volume of reagent to support a particular reaction.

The dilutor/dispenser unit is usually pre-set to aspirate a predetermined volume of sample and, also, to dispense a predetermined volume of diluent. During the aspiration, or sample-loading cycle, a "short" sample can result, which may be unnoticed by the technician. Such "short" sample can result, for example, from the malfunction of the aspirating pump, momentary and unintentional withdrawal of the aspirating probe from the sample liquid, a clogging of the probe inlet, etc.

3. Objects of the Invention

An object of this invention is to provide improved method and apparatus for dispensing precise liquid volumes. Another object of this invention is to provide improved dispenser apparatus which operates to provide a visual indication or an alarm automatically upon aspiration of an improper liquid volume, i.e., a "short" sample. A still further object of this invention is to provide a dilutor/dispenser apparatus which is reliable in operation and suitable for unattended operation.

SUMMARY OF THE INVENTION

The present invention is directed to method and apparatus for detecting, either automatically or visually, the occurrence of a "short" sample in a dilutor/dispenser unit. The present invention contemplates the introduction of a positive marker at the probe inlet immediately prior to each sample aspiration cycle. In the preferred embodiment of the invention, the marker is an air bubble, or segment. Aspiration of the sample displaces the marker along the probe system. The position of such marker along the probe system and, also, the presence of liquid sample at the probe inlet are detected prior to the dispense cycle, to ensure the aspiration of a proper sample volume for subsequent dispensing. The probe system is calibrated, such that the location of the bubble along the probe system is indicative of the volume of sample which has been aspirated.

A BRIEF DESCRIPTION OF THE DRAWINGS

FIGS. 1A and 1B illustrate a dilutor/dispenser apparatus embodying the principles of the invention.

FIGS. 2A 2E serve to further illustrate the operation of the system illustrated in FIG. 1A.

DETAILED DESCRIPTION OF THE INVENTION

Figure 1A:
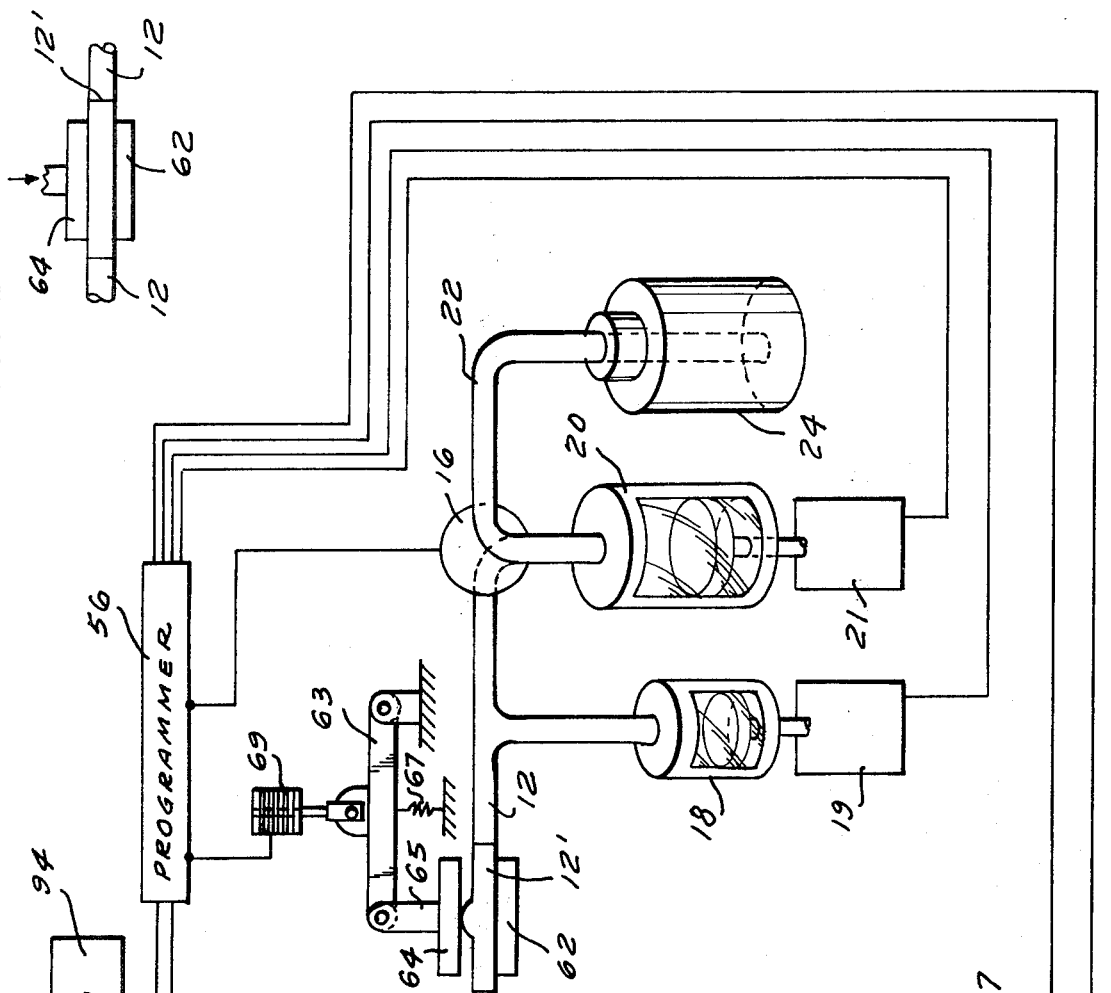

Referring now to the drawings, the present invention comprises a dilutor/dispenser arrangement 10, comprising a tube 12 connected at one end to probe 14 and at its other end to one port of a three-port, two position valve 16. At least, the inlet end of probe 14 is formed of transparent material. A sample piston pump 18 is connected to tube 12. A reagent piston pump 20 is connected to a second port of valve 16. Drive motors 19 and 21 are connected to sample pump 18 and reagent pump 20, respectively. The remaining port of valve 16 is connected along tube 22 to a source of diluent 24. The structure, so far described, is common to many types of prior art dilutor/dispenser arrangements.

Also, a plurality of sample receptacles 26, containing sample liquids to be analyzed, and a plurality of reaction cells 28 are positioned in alternating fashion on a turntable 30. Turntable 30 is removably mounted on a shaft 32, supported in a bearing 34 contained in a horizontal plate 36 located within housing 37. Plate 36 supports on its undersurface a motor 38, which is mechanically coupled through such plate to a drive gear 40 adapted to engage a Geneva-drive gear 42 coupled to shaft 32, so as to index turntable 30 in the direction indicated by the arrow. Also, plate 36 is adapted to be elevated or lowered by means of a screw gear 44 mechanically coupled to a reversible motor 46 fixedly mounted on the bottom wall 54 of housing 37. Screw gear 44 engages an internally threaded member 48 fixedly mounted on plate 36. Also, the remote end of plate 38 is adapted to receive guide rods 50, whose ends are received in the top and bottom walls 52 and 54 of housing 37.

As hereafter described, motor 38 is controlled to index turntable 30, so as to locate either a receptacle 26 or a cell 28 immediately below the probe 14. Also, reversible motor 46 is controlled between successive indexings of turntable 30, as hereafter described, to raise and lower such turntable, so as to locate the inlet end of probe 14 within a receptacle 26 (during the aspiration cycle) or a cell 28 (during the dispense cycle). It should be appreciated that the described mechanism is merely illustrative of numerous mechanisms available to position successive sample receptacles 26 and reaction cells 28, in turn, with respect to probe 14.

The operation of the dilutor/dispenser arrangement 10 is controlled by a programmer 56. Prior to initiating operation, a technician would load a plurality of sample receptacles 26, each containing a liquid sample to be analyzed, and reaction cells 28 onto turntable 30. Such loading may be effected either while turntable 30 is in a lowered position or is removed from shaft 32.

Cells 28 are preferably adapted to perform a particular methodology with respect to the samples contained in the receptacle 26 presented immediately priorly to probe 14. Cells 28 can be of the type described in U.S. Pat. No. 4,043,678, issued on Aug. 23, 1977 and assigned to a same assignee. As shown, each cell 28 contains the necessary reagent 58, which may be lyophilized, to perform a desired analysis, of the sample liquid. When a turntable 30 has been loaded and positioned with a receptacle 26 located beneath probe 14, the technician will instruct programmer 56. Programmer 56 operates reversible motor 46 to rotate threaded member 48, so as to elevate turntable 30 and immerse probe 14 within the sample liquid contained in receptacle 26. While probe 14 is so immersed, programmer 56 operates drive motor 19 to withdraw sample pump 18 and aspirate a given sample volume along probe 14 and tube 12. The aspirated sample volume is equal to the displacement of such pump but insufficient to completely fill tube 12, whereby the sample pump 18 remains filled with diluent. At this time, reagent pump 20 has been withdrawn, so as to be filled with diluent, as hereafter described. Subsequent to the aspiration cycle, programmer 56 operates motor 46, in a reverse direction, to lower turntable 30 and withdraw probe 14 from receptacle 26. When probe 14 has been withdrawn, programmer 56 operates motor 38, which causes drive gear 40 to engage Geneva-type gear 42 and rotate turntable 30 to locate the adjacent cell 28 beneath probe 14.

When cell 28 has been located beneath probe 14, programmer 56 operates reversible motor 46 to elevate turntable 30, such that probe 14 passes through the cover 60 and locates within such cell. Cover 60 serves to seal cell 28 and, preferably, comprises a multi-ply structure, one ply comprising an absorbant layer for wiping the outer surfaces of probe 14, to prevent contamination between successive samples. Programmer 56 subsequently operates drive motors 19 and 21 to return sample pump 18 and diluent pump 20, such as to dispense liquids contained along tube 12 and probe 14 into cell 28. The quantity of liquid, that is, sample and diluent, dispensed into cell 28 is equal to the combined controlled forward displacements of the sample pump 18 and diluent pump 20. As such, predetermined volumes of both sample and diluent are introduced in cell for reaction with the lyophilized reagent 58. The reaction mixture can be subsequently analyzed, e.g., colorimetrically. For example, the plurality of cells 28, when loaded, can be loaded in a magazine and successively introduced into a system, such as described in the above-identified U.S. Pat. No. 3,971,630.

Following the dispense cycle, valve 16 is controlled by programmer 56, to connect diluent pump 20 along tubing 22 to diluent source 24. At this time, programmer 56 operates drive motor 21 to withdraw diluent pump 20, so as to aspirate diluent and be primed for a next operation. Valve 16 is subsequently normalized by programmer 56, as indicated in dashed outline.

Figure 1B:
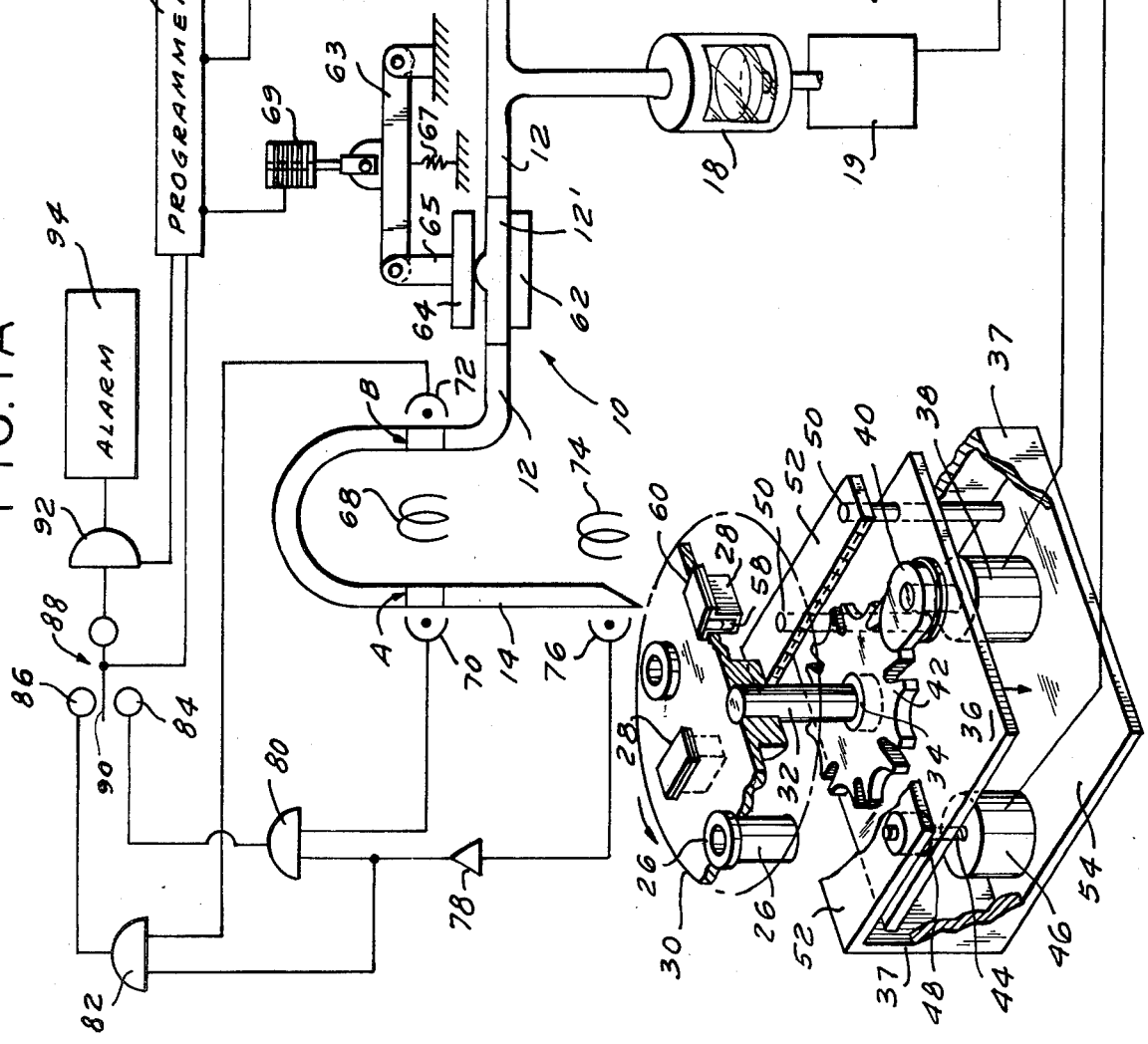
Figure 2A:
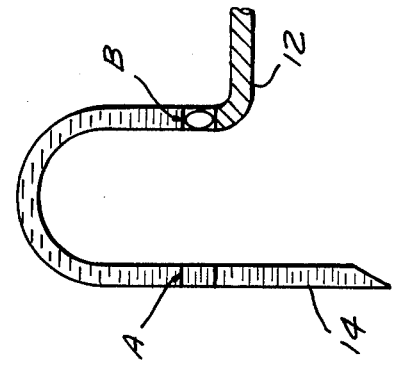

The structure and operation, so far described, of the dilutor/dispenser arrangement 10 are conventional. However, such apparatus does not make provision for the detection of a "short" sample. To detect a "short" sample, a section 12' of tube 12 is formed of flexible resilient material and defines a resilient bulbous portion. The bulbous portion of tube section 12' is positioned between an anvil 62 and a hammer 64. An arm 63, fixed at one end, is pivotly connected at the other end to an extension 65 of hammer 64. Normally, arm 63 is biased by spring 67 to hammer 64 depressed, as shown in FIG. 1B. Arm 63 is mechanically coupled to the plunger of a solenoid 69. Immediately prior to each aspiration cycle, however, programmer 56 energizes solenoid 69 to raise hammer 64, whereby the bulbous portion of tube section 12' extends, so as to increase the volume of tube 12. As tube 12 is filled with diluent, following the previous dispense cycle, a small air segment 66, or marker, is aspirated into probe 14, as shown in FIG. 2A. It is evident that any arrangement, e.g., a solenoid operated piston, bellow, etc., operative to momentarily increase the volume or capacity, of the tube 12/probe 14 combination can be used to introduce such marker. The volume of the aspirated air segment 66 is preferably of very small volume, e.g., one or two $\lambda$ and sufficient to occlude tube 12. Accordingly, during the aspiration cycle, the air bubble 66 is displaced along probe 14 and tube 12 by the aspirated liquid. By graduating tube 12, the displacement of air bubble 66 along tube 12 is indicative of the sample volume which has been aspirated. For example, at least portions A and B of tube 12 are formed of a transparent material and correspond to the location of air bubble 66 when predetermined sample volumes, e.g., 10 $\lambda$ and 50 $\lambda$ respectively, have been aspirated. Preferably, the length of portions A and B are equal to the length of the air segment 66.

Figure 2B:
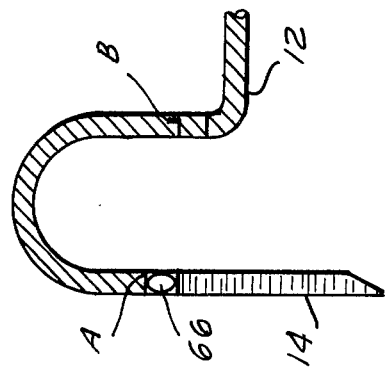
Figure 2C:
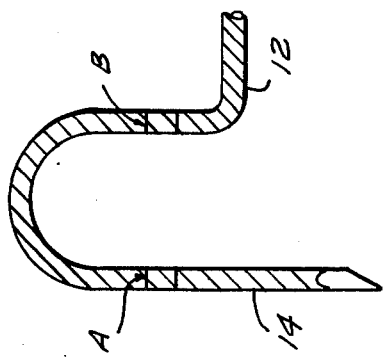
Figure 2D:
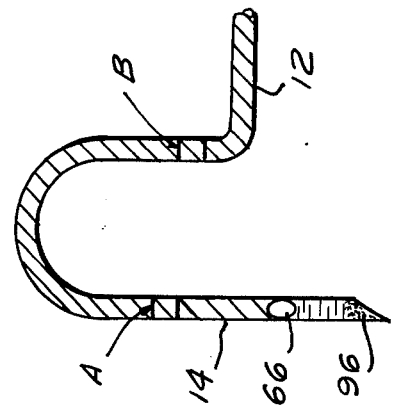

For example, FIGS. 2B and 2C illustrate normal 10 $\lambda$ and 50 $\lambda$ aspiration cycles, respectively, tube 12 and probe 14 upstream of portions A and B, respectively, being filled with sample liquid and an air bubble 66 being located at portions A and B, respectively. It is evident that location of air segment 66 at other than locations A or B is indicative of other than 10 $\lambda$ or 50 $\lambda$ sample volumes, respectively, having been aspirated. Additionally, the location of an air segment at the inlet of probe 14, as illustrated in FIG. 2D, is further indicative of a "short" sample aspiration.

The proper location of air bubble 66 can be detected by conventional optical or conductivity techniques. For example, an optical arrangement is illustrated for detecting the presence of an air bubble 66 at either locations A or B and, concurrently, at the inlet of probe 14, which provides an alarm, or equivalent indication, whenever an improper sample volume has been aspirated. In such arrangement, light source 68 is positioned to illuminate transparent portions A and B of tube 12, transmitted light being detected by detectors 70 and 72, respectively. Also, a light source 74 is positioned to illuminate the transparent inlet portion of probe 14, transmitted light being detected by detector 76.

As is known, a conduit having transparent walls, when filled with a transmissive liquid, will act as a cylindrical lens; on the other hand, a same conduit filled with air acts to scatter light, because of the mismatch between the respective indices of refraction of the air and the material forming walls of the conduit and, also, due to the curvature of such walls. Accordingly, when an air bubble 66 is located between a light source and its corresponding detector, the light incident on such detector, is significantly greater than when such portions are filled with liquid. To this end, the characteristics of detectors 70 and 72 and, also, detector 76 are determined to be energized only when liquid is located therebetween and their corresponding light sources.

The output of detector 76 is connected to the input of an inverter circuit 78. Also, the output of detectors 70 and 72 are connected to one input of OR gates 80 and 82, respectively. The output of inverter circuit 78 is connected to the remaining inputs of OR gates 80 and 82, respectively. The outputs of OR gates 80 and 82 are connected to terminals 84 and 86, respectively, of switch 88. The pole 90 of switch 88 is selectively connectable to terminal 84 or 86 by programmer 56, when 10 λ or 50 λ samples, respectively, are to be aspirated and dispensed. Pole 90 is connected along an enable gate 92 to an alarm circuit 94. Gate 92 is enabled by programmer 56 at the completion of each aspiration cycle and before the dispense cycle.

The presence of an air bubble 66 at portion A or B of tube 12 and the concurrent presence of liquid at the inlet of probe 14, indicating the proper aspiration of a 10 λ sample and a 50 λ sample, respectively, is ineffective to actuate alarm 94, when gate 92 is enabled by programmer 56. FIGS. 2B and 2C illustrate the proper location of an air segment 66 at portions A and B, respectively, together with the presence of sample liquid at the inlet of probe 14, upon proper aspiration of a 10 λ sample and a 50 λ sample. For example, in the case of a proper 10 λ sample aspiration, detector 72 is energized while detector 70 is unenergized. Pole 90 of switch 88 is connected to terminal 84 by programmer 56. While detection 76 is energized, OR gate 80 is not operated because of the presence of inverter 78, and alarm 94 is not sounded when gate 92 is enabled by programmer 56 at the completion of the aspiration cycle. Similarly, in the case of a proper 50 λ sample aspiration, while pole 90 is connected to terminal 86 of switch 88, neither OR gate 82 or gate 92 are operated, when the latter is enabled by programmer 56 at the completion of the aspiration cycle. In the event that alarm 94 is not operated, programmer 56 commences the dispense cycle, as described, to dispense the sample liquid into cell 28.

However, if an air segment is not present at positions A or B of tube 12 at the completion of a 10 λ or 50 λ aspiration cycle, respectively, and, concurrently, probe 14 is not completely filled with sample, gate 92 would be operated, when enabled by programmer 56, whereby alarm 94 would be sounded. Similarly, with respect to either aspiration cycle, the presence of an air segment at the inlet of probe 14 would energize gate 80 and operate alarm 94.

Figure 2E:
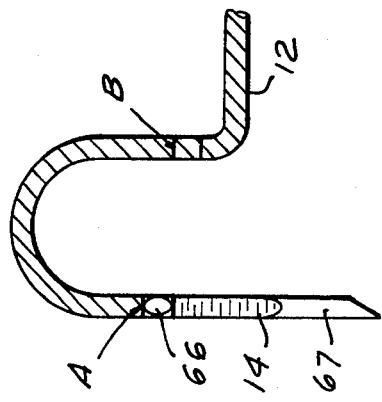

FIGS. 2D and 2E illustrate "short" sample conditions, following 10 λ sample aspiration cycles, which would result in the operation of alarm 94. FIG. 2D illustrates the condition wherein the inlet end of probe 14 is filled with air 67, rather than sample liquid and an air bubble 66 is located at portion A of tube 12. Accordingly, detector 76 is unenergized and detector 70 is energized. Because of inverter 78, however, both gates 80 and 92 would be operated to sound alarm 94, when gate 92 is enabled by programmer 56. Also, FIG. 2E illustrates the condition resulting from a clogging or probe 14 by debris or a clot 96. In such event, the air bubble 66 would be displaced less than normal along probe 14 and tube 12, such that detector 70 would be energized, detector 76 remaining unenergized, such as to sound alarm 94, when gate 92 is enabled by programmer 56. If the inlet of probe 14 is clogged with a clot 96, simulating the presence of an air segment, such condition would be sufficient to concurrently energize detector 76. A similar operation would result with respect to a 50 λ aspiration cycle when pole 90 is connected to terminal 86, whereby OR gates 82 and 92 would be operated, rather than OR gates 80 and 92, as described.

What is claimed is:

1. A system comprising a probe system, means for introducing a marker at an inlet of said probe system, means for aspirating a predetermined volume of liquid into said probe system, said marker being displaceable along said probe system upon aspiration of liquid therein, said probe system being calibrated such that the displacement of said marker is indicative of the volume of liquid aspirated therein, and means for dispensing said aspirated liquid.

2. A system as defined in claim 1, wherein said marker is an air bubble.

3. A system as defined in claim 2, wherein said introducing means comprises means for increasing the volume of said probe system prior to aspiration of said liquid.

4. A system as defined in claim 3, wherein a portion of said probe system is formed of a resilient material, and said introducing means includes means for increasing the volume of said portion prior to aspiration of said sample.

5. A system as defined in claim 3, wherein a portion of the probe system is formed of a resilient material, and said introducing means comprises means for compressing and releasing said resilient portion, whereby an air bubble is aspirated at said probe inlet prior to aspiration of said liquid.

6. A system as defined in claim 1, further comprising means for immersing said probe inlet into liquid contained in a first receptacle to aspirate liquid therefrom and for dispensing said aspirated liquid into a second receptacle.

7. A system as defined in claim 6, wherein said probe system normally contains a diluent, said dispensing means being operative to dispense said aspirated liquid along with a predetermined volume of said diluent into said second receptacle.

8. A system as defined in claim 6, wherein said second receptacle contains a reagent for reacting with said dispensed liquid.

9. A system as defined in claim 8, wherein said reagent is lyophilized.

10. A system as defined in claim 9, further including means for operating said introducing means prior to immersion of said probe system inlet into each of said first receptacles.

11. A system as defined in claim 1, wherein said probe system includes a transparent portion disposed at a predetermined distance from said probe system inlet, said marker being displaceable to said transparent portion upon aspiration of predetermined liquid volume.

12. A system as defined in claim 1, further comprising means for supporting a plurality of first receptacles containing liquid to be aspirated and a plurality of second receptacles for dispensing liquid, and means for relatively positioning said probe system inlet with respect to alternate ones of said first and second receptacles, said positioning means including means to immerse said probe system inlet into successive ones of said first receptacles.

13. A system as defined in claim 12, further including means to cleanse the exterior portions of said probe system inlet subsequent to immersion into each of said first receptacles.

14. Apparatus as defined in claim 1, further includes means for detecting the location of said marker along said probe system.

15. A system as defined in claim 14, wherein said marker detecting means includes means for actuating an alarm.

16. An apparatus as defined in claim 14, wherein said detecting means includes a first means for optically detecting said marker at said transparent portion.

17. A system as defined in claim 16, wherein said means for optically detecting said marker comprises a light source and a first light sensing detector disposed adjacent said light source and said transparent portion.

18. A system as described in claim 17, wherein said detecting means further includes a second detector for detecting the presence of air at said probe inlet following aspiration of said liquid volume.

19. A system as defined in claim 18, further including logic means operatively connected to and responsive to said first and second detectors, and means operatively connected to and responsive to said logic means for actuating an alarm.

20. A method for determining the aspiration of a predetermined volume of liquid into a dilutor/dispenser system, said dilutor/dispenser system including a probe system, said method comprising the steps of:

filling said probe system with a diluent to be dispensed along with a predetermined volume of liquid, introducing a marker at the inlet of said probe system, aspirating a volume of said liquid to displace said marker along said probe system, detecting the location of said marker along said probe system to ascertain the volume of said liquid which has been aspirated, and dispensing said aspirated volume of said liquid along with said marker and a predetermined volume of said diluent in accordance with said marker location.

* * * * *